United States Patent
Fuchs et al.

[11] 4,388,322
[45] Jun. 14, 1983

[54] COMBATING PESTS WITH SUBSTITUTED 3-(1,2-DIBROMO-ALKYL)-2,2-DIMETHYL-CYCLOPROPANE-1-CARBOXYLIC ACID ESTERS

[75] Inventors: Rainer Fuchs, Wuppertal; Klaus Naumann, Leverkusen; Ingeborg Hammann, Cologne; Wilhelm Stendel, Wuppertal, all of Fed. Rep. of Germany

[73] Assignee: Bayer Aktiengesellschaft, Leverkusen, Fed. Rep. of Germany

[21] Appl. No.: 226,290

[22] Filed: Jan. 19, 1981

[30] Foreign Application Priority Data

Feb. 5, 1980 [DE] Fed. Rep. of Germany ....... 3004092

[51] Int. Cl.³ .................... A01N 37/34; C07C 121/75
[52] U.S. Cl. ................................ 424/304; 260/465 D; 260/544 D; 260/544 S; 424/278; 424/282; 424/308; 549/362; 549/366; 549/442; 549/447; 560/9; 560/55; 560/105; 562/426; 562/465; 562/496
[58] Field of Search ..................... 260/465 D, 544 D; 560/9, 124, 55, 105; 424/304, 305, 308, 278, 282; 549/365, 366, 442, 447; 562/426, 465, 496

[56] References Cited

U.S. PATENT DOCUMENTS

| | | | |
|---|---|---|---|
| 4,157,397 | 6/1979 | Engel | 260/465 D X |
| 4,224,227 | 9/1980 | Martel | 560/124 X |

FOREIGN PATENT DOCUMENTS

| | | |
|---|---|---|
| 6600 | 6/1979 | European Pat. Off. . |
| 15239 | 1/1980 | European Pat. Off. . |
| 2364884 | 9/1976 | France . |
| 2398041 | 7/1977 | France . |
| 2398457 | 7/1977 | France . |
| 2380246 | 2/1978 | France . |
| 2380247 | 2/1978 | France . |
| 2380248 | 2/1978 | France . |
| 2419932 | 3/1978 | France . |
| 2428396 | 6/1979 | France . |

*Primary Examiner*—Dolph H. Torrence
*Attorney, Agent, or Firm*—Sprung, Horn, Kramer & Woods

[57] ABSTRACT

Substituted 3-(1,2-dibromo-alkyl)-2,2-dimethyl-cyclopropane-1-carboxylic acid esters of the formula

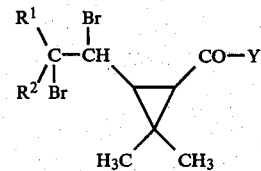

in which
$R^1$ is halogen or optionally substituted phenyl or optionally substituted alkyl,
$R^2$ is hydrogen, halogen or optionally substituted alkyl, and
Y is the radical of an alcohol customary in pyrethroids, with the proviso that Y is a benzyloxy radical which is substituted by halogen and optionally substituted by at least one additional radical if $R^1$ is halogen or methyl, which possess pesticidal properties. The acid moieties of such esters wherein $R^1$ is optionally substituted phenyl are new compounds.

9 Claims, No Drawings

COMBATING PESTS WITH SUBSTITUTED 3-(1,2-DIBROMO-ALKYL)-2,2-DIMETHYL-CYCLOPROPANE-1-CARBOXYLIC ACID ESTERS

The present invention relates to certain new substituted 3-(1,2-dibromo-alkyl)-2,2-dimethyl-cyclopropane-1-carboxylic acid esters, to a process for their preparation and to their use as agents for combating pests, especially as insecticides and acaricides; it also relates to new intermediate products for the preparation of the new esters.

It is known that certain cyclopropanecarboxylic acid esters, for example 3-(2,2-dichloro-vinyl)-2,2-dimethyl-cyclopropane-1-carboxylic acid 3-phenoxy-benzyl ester and 3-phenoxy-α-cyano-benzyl ester have insecticidal and acaricidal properties (see U.S. Pat. Nos. 4,024,163 and 4,031,239). However, the action of these compounds is not always satisfactory, especially in the case of low concentrations of active compound and when small amounts are applied.

The present invention now provides:

(1), as new compounds, the substituted 3-(1,2-dibromoalkyl)-2,2-dimethyl-cyclopropane-1-carboxylic acid esters of the general formula

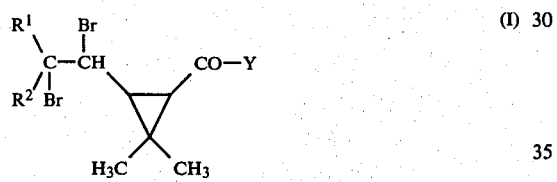

in which
$R^1$ represents halogen, optionally substituted phenyl or optionally substituted alkyl,
$R^2$ represents hydrogen, halogen or optionally substituted alkyl and
Y represents the radical of an alcohol customary in pyrethroids, with the proviso that Y represents a benzyloxy radical which is substituted by halogen and optionally substituted by one or more other radicals if $R^1$ represents halogen or methyl;

(2) a process for the preparation of a compound of the formula (I), characterized in that (a) a 3-alkenyl-2,2-dimethyl-cyclopropane-1-carboxylic acid ester of the general formula

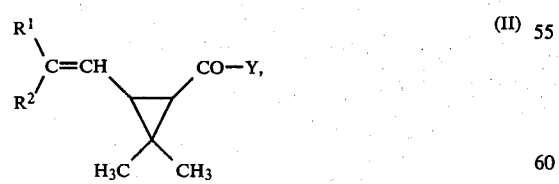

in which
$R^1$, $R^2$ and Y have the abovementioned meanings, is reacted with bromine, if appropriate in the presence of a diluent, or (b) a 3-(1,2-dibromo-alkyl)-2,2-dimethyl-cyclopropane-1-carboxylic acid of the general formula

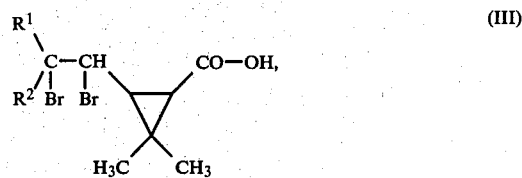

in which
$R^1$ and $R^2$ have the abovementioned meanings, or a reactive derivative thereof, is reacted with an alcohol customary in pyrethroids, of the general formula $$Y\text{—}H \qquad (IV),$$

in which
Y has the abovementioned meaning, or with a reactive derivative thereof, if appropriate in the presence of an acid-binding agent, if appropriate in the presence of a catalyst and if appropriate in the presence of a diluent;

(3), as new compounds, the 3-(1,2-dibromo-alkyl)-2,2-dimethyl-cyclopropane-1-carboxylic acid derivatives of the general formula

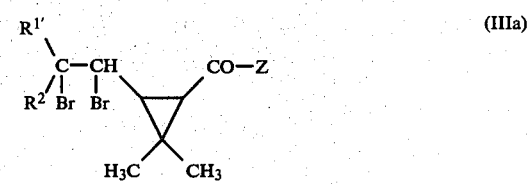

in which
$R^2$ has the meaning given under (1),
$R^{1'}$ represents optionally substituted phenyl and
Z represents hydroxyl, chlorine, $C_1$-$C_4$-alkoxy or $O^{\ominus}M^{\oplus}$,
wherein
$M^{\oplus}$ represents an ammonium ion or one alkali metal or akaline earth metal ion equivalent;
and (4) a process for the preparation of a compound of the formula (IIIa), characterized in that a 3-alkenyl-2,2-dimethyl-cyclopropane-1-carboxylic acid of the general formula

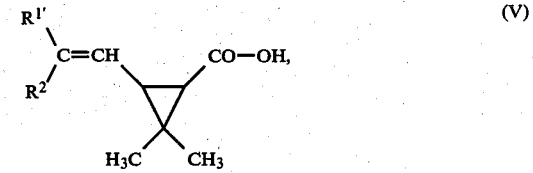

in which
$R^1$ and $R^2$ have the abovementioned meanings, is reacted with bromine, if appropriate in the presence of a diluent, and the bromination product is optionally converted into another carboxylic acid derivative of the formula (IIIa) by any customary method.

The new substituted 3-(1,2-dibromo-alkyl)-2,2-dimethyl-cyclopropane-1-carboxylic acid esters are distinguished by a high insecticidal and acaricidal activity.

Surprisingly, the compounds of the formula (I) according to the invention exhibit a considerably more powerful insecticidal and acaricidal action than the compounds of analogous structure and the same type of action which are known from the state of the art.

Preferred compounds of the formula (I) are those in which

R$^1$ represents phenyl which is optionally substituted by halogen and/or by one or more optionally halogen-substituted radicals selected from C$_1$–C$_4$-alkyl, C$_1$–C$_4$-alkoxy, C$_1$–C$_4$-alkylthio or C$_1$–C$_2$-alkylene-dioxy radicals, or represents optionally halogen-substituted C$_1$–C$_4$-alkyl or halogen, R$^2$ represents hydrogen, halogen or optionally halogen-substituted C$_1$–C$_4$-alkyl and Y represents the radical

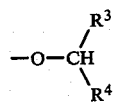

wherein

R$^3$ represents hydrogen, cyano or optionally substituted alkyl, alkenyl or alkynyl and R$^4$ represents phenyl which is substituted by halogen and/or by phenoxy which is itself optionally substituted by halogen, alkyl or halogenoalkyl, with the proviso that the phenyl radical contains at least one halogen substituent if R$^1$ represents methyl or halogen.

Particularly preferably,

R$^3$ represents hydrogen or cyano and

R$^4$ represents pentafluorophenyl, pentachlorophenyl, 4-fluoro-3-phenoxy-phenyl or 4-fluoro-3-(4-fluoro-phenoxy)-phenyl or, provided that R$^1$ represents optionally substituted phenyl, represents 3-phenoxyphenyl or 3-(4-fluoro-phenoxy)-phenyl.

If, for example, 3-(2,2-dibromo-vinyl)-2,2-dimethyl-cyclopropane-1-carboxylic acid 4-fluoro-3-phenoxy-benzyl ester is used as the starting substance in the process variant described under (2a) for the preparation of the compounds of the formula (I), the bromination reaction can be outlined by the following equation:

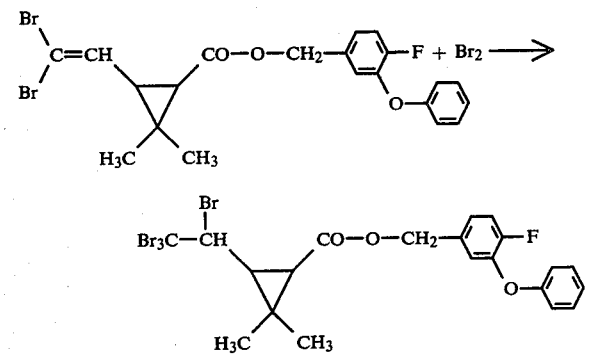

Formula (II) provides a definition of the 3-alkenyl-2,2-dimethyl-cyclopropane-1-carboxylic acid benzyl esters to be used as starting substances for process variant (2a). Preferably, in this formula, R$^1$, R$^2$ and Y represent those radicals which have already been mentioned as preferred in the definition of the radicals R$^1$, R$^2$ and Y in formula (I).

Examples of the starting substances of the formula (II) which may be mentioned are: 3-(2,2-difluoro-vinyl)-, 3-(2,2-dichloro-vinyl)-, 3-(2,2-dibromo-vinyl)-, 3-(2-phenyl-vinyl)-, 3-(2-chloro-2-phenyl-vinyl)-, 3-(2-chloro-2-(4-chloro-phenyl)-vinyl)- and 3-(2-bromo-2-(4-chloro-phenyl)-vinyl)-2,2-dimethyl-cyclopropane-1-carboxylic acid 4-fluoro-3-phenoxy-benzyl ester and 4-fluoro-3-phenoxy-α-cyano-benzyl ester.

Compounds of the formula (II) are already known (see DE-OS (German Published Specifications) Nos. 2,709,264 and 2,730,515 and Chem. Soc. Review Volume 7/4 (1978) page 473 et seq.).

Process variant (2a) is preferably carried out using a diluent. Possible diluents are virtually any of the organic solvents which are inert towards bromine. These include, as preferences, aliphatic halogenated hydrocarbons, for example methylene chloride, chloroform, carbon tetrachloride and 1,2-dichloroethane.

The reaction temperature is kept between −20° and +80° C., preferably between 0° and 50° C., in process variant (2a). The process is in general carried out under normal pressure.

The starting substances are usually employed in equimolar amounts for carrying out process variant (2a). An excess of one or the other of the reactants provides no substantial advantages. The reaction is in general carried out in a suitable diluent and the reaction mixture is stirred at the required temperature for several hours. The reaction solution is then washed with water and the solvent is subsequently carefully distilled off from the organic phase under reduced pressure and at moderately elevated temperature ("incipient distillation"), the product in general being obtained as an oily residue.

If, for example, 3-(1,2-dibromo-2-chloro-2-phenyle-thyl)-2,2-dimethyl-cyclopropane-1-carboxylic acid chloride and 3-phenoxy-α-cyano-benzyl alcohol are used as starting substances in the process variant described under (2b) for the preparation of compounds of the formula (I), the reaction of these compounds can be outlined by the following equation:

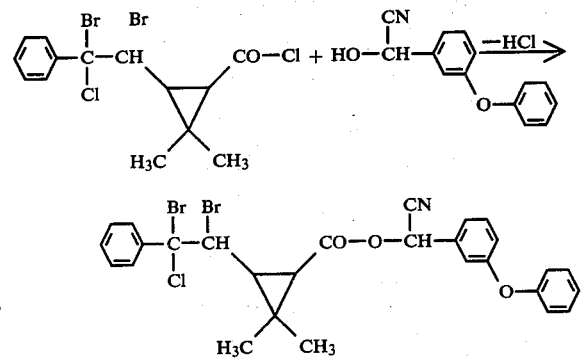

Formula (III) provides a definition of the 3-(1,2-dibromoalkyl)-2,2-dimethyl-cyclopropane-1-carboxylic acids to be used as starting substances for process variant (2b).

Preferably, in this formula, R$^1$ and R$^2$ represent those radicals which have been mentioned as preferred in the definition of the radicals R$^1$ and R$^2$ in formula (I). Particularly preferred starting substances are the new compounds of the formula (IIIa) in which, preferably, R$^2$ represents hydrogen, halogen or optionally halogen-substituted alkyl, R$^{1'}$ represents phenyl which is optionally substituted by halogen and/or by one or more optionally halogen-substituted radicals selected from C$_1$–C$_4$-alkyl, $C_1$–$C_4$-alkoxy, $C_1$–$C_4$-alkylthio and $C_1$–$C_2$-alkylenedioxy radicals and Z represents hydroxyl, chlorine, $C_1$–$C_4$-alkoxy or $O^\ominus M^\oplus$, wherein $M^\oplus$ represents an ammonium ion or one alkali metal or alkaline earth metal ion equivalent.

Examples of the starting substances of the formula (III) or (IIIa) which may be mentioned are:

3-(1,2-dibromo-2-phenyl-ethyl)-, 3-(1,2-dibromo-2-(4-chlorophenyl)-ethyl)-, 3-(1,2-dibromo-2-chloro-2-phenyl-ethyl)-, 3-(1,2-dibromo-2-chloro-2-(4-chlorophenyl)-ethyl)-3-(1,2-dibromo-2-chloro-2-(4-fluorophenyl)-ethyl)-, 3-(1,2-dibromo-2-chloro-2-(4-trifluoromethoxy-phenyl)-ethyl)- and 3-(1,2,2-tribromo-2-(4-chloro-phenyl)-ethyl)-2, 2-dimethyl-cyclopropane-1-carboxylic acid and the corresponding acid chlorides, methyl esters and ethyl esters.

The new carboxylic acids of the formula (IIIa) are obtained by the process described above under (4), by reacting 3-alkenyl-2,2-dimethyl-cyclopropane-1-carboxylic acids of the formula (V) above, in which, preferably, $R^2$ represents hydrogen, halogen or optionally $R^{1'}$ represents phenyl which is optionally substituted by halogen and/or by one or more optionally halogen-substituted radicals selected from $C_1$–$C_4$-alkyl, $C_1$–$C_4$-alkoxy, $C_1$–$C_4$-alkylthio and $C_1$–$C_2$-alkylenedioxy radicals, with bromine, preferably in an inert solvent, for example carbon tetrachloride, at temperatures between 0° and 50° C.

The corresponding acid chlorides can be prepared from the resulting acids of the formula (IIIa) by customary methods, for example by reaction with thionyl chloride at temperatures between 10° and 100° C., if appropriate using a diluent, for example carbon tetrachloride.

The esters are likewise obtained from the acid chlorides of the formula (IIIa) by customary methods, for example by reaction with alcohols, for example methanol or ethanol, if appropriate in the presence of an acid-binding agent, for example pyridine, at a temperature between 10° and 50° C. The salts of the formula (IIIa) are obtained from the corresponding acids by reaction with ammonia or amines or alkali metal hydroxides or alkaline earth metal hydroxides, for example potassium hydroxide, if appropriate using a diluent, for example water, methanol or ethanol, at a temperature between 10° and 50° C.

The precursors of the formula (V) are known compounds (see DE-OS (German Published Specification) No. 2,730,515 and U.S. Pat. No. 4,157,447).

Formula (IV) provides a definition of the alcohols also to be used as starting substances in process variant (2b). Preferably, in this formula, Y represents those radicals which have been mentioned as preferred in the definition of Y in formula (I).

Examples of the starting substances of the formula (IV) which may be mentioned are: 3-phenoxy-benzyl alcohol, α-cyano-3-phenoxy-benzyl alcohol, 4-fluoro-3-phenoxy-benzyl alcohol, 4-fluoro-3-phenoxy-α-cyano-benzyl alcohol, 3-(4-fluoro-phenoxy)-benzyl alcohol and 3-(4-fluoro-phenoxy)-α-cyano-benzyl alcohol.

The starting compounds of the formula (IV) are known (see DE-OS (German Published Specifications) Nos. 2,621,433 and 2,709,264 and Chem. Soc. Review Volume 7/4 (1978) page 473 et seq.).

Process variant (2b) is preferably carried out using a diluent. Possible diluents are virtually any of the inert organic solvents. These include, as preferences, aliphatic and aromatic, optionally halogenated hydrocarbon, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene; ethers, such as diethyl ether, dibutyl ether, glycol dimethyl ether, diglycol dimethyl ether, tetrahydrofuran and dioxane; ketones, such as acetone, methyl ethyl ketone, methyl isopropyl ketone and methyl isobutyl ketone; esters, such as methyl acetate and ethyl acetate; nitriles, for example acetonitrile and propionitrile; amides, for example dimethylformamide, dimethylacetamide and N-methylpyrrolidone; and dimethylsulphoxide, tetramethylene sulphone and hexamethylphosphoric acid triamide.

Possible acid acceptors are any of the customary acid-binding agents. Acid-binding agents which have proved particularly suitable are alkali metal carbonates and alcoholates, such as sodium carbonate and potassium carbonate and sodium methylate or ethylate and potassium methylate or ethylate, and aliphatic, aromatic or heterocyclic amines, for example triethylamine, trimethylamine, dimethylaniline, dimethylbenzylamine and pyridine.

The reaction temperature can be varied within a substantial range. In general, the reaction is carried out between 0° and 100° C., preferably at from 10° to 50° C.

Process variant (2b) is in general carried out under normal pressure.

The starting substances are usually employed in equimolar amounts for carrying out the process variant (2b). An excess of one or other of the reactants provides no substantial advantages. The reaction is in general carried out in a suitable diluent in the presence of an acid acceptor and the reaction mixture is stirrred at the required temperature for several hours. The reaction mixture is then poured into water, the organic phase is separated off, if appropriate after adding a water-immiscible solvent, for example toluene, and shaking thoroughly, and is washed with water, dried and filtered and the solvent is distilled off from the filtrate under reduced pressure.

The compounds of the formula (I) are obtained in the form of oils, some of which cannot be distilled without decomposition, but can be freed from the last volatile constituents by so-called "incipient distillation," that is to say by prolonged heating to moderately elevated temperatures under reduced pressure, and can be purified in this manner. They are characterized by their refractive index or their $^1$HNMR spectrum.

In addition to process variants (2a) and (2b) described above, other possible methods for preparing compounds of the formula (I) which are not described in more detail here but which are to be mentioned are the reaction of lower alkyl esters of carboxylic acids of the formula (III) with alcohols of the formula (IV), reaction of salts of carboxylic acids of the formula (III) with benzyl halides, as reactive derivatives of alcohols of the formula (IV), and the reaction of chlorides of carboxylic acids of the formula (III) with benzaldehydes, which are derived from benzyl alcohols of the formula (IV) in the presence of alkali metal cyanides.

PREPARATIVE EXAMPLES

Example 1

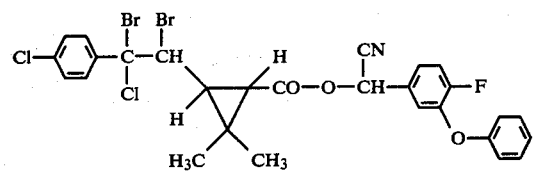 (1)

5.1 g (0.01 mol) of trans-3-(E,Z,-2-chloro-2-(4-chlorophenyl)-vinyl)-2,2-dimethyl-cyclopropane-1(R,S)-carboxylic acid α-(R,S)-cyano-3-phenoxy-4-fluoro-benzyl ester were dissolved in 50 ml of carbon tetrachloride, and 1.6 g (0.01 mol) of bromine, dissolved in 10 ml of carbon tetrachloride, were added dropwise at 20°14 25° C., whilst stirring. Thereafter, the reaction mixture was subsequently stirred at room temperature for 12 hours and was then extracted by shaking once with 100 ml of water; the organic phase was separated off and the solvent was stripped off under a waterpump vacuum. The residue was freed from the last traces of solvent by brief incipient distillation at 60° C./2 mbar. 5.9 g (88% of theory) of trans-3-(2-chloro-2-(4-chloro-phenyl)-1,2-dibromoethyl)-2,2-dimethyl-cyclopropane-1-(R,S)-carboxylic acid α-(R,S)-cyano-3-phenoxy-4-fluorobenzyl ester were obtained was a very viscous oil.

The structure was confirmed by the $^1$H-NMR spectrum.

$^1$H-NMR spectrum (in CDCl$_3$/TMS):

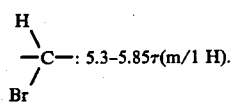

Example 2

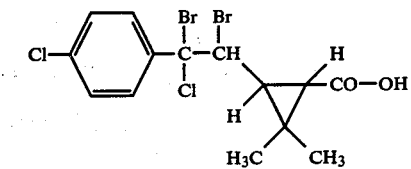 (a)

14 g (0.0492 mol) of trans-3-(E,Z-2-chloro-2-(4-chlorophenyl)-vinyl)-2,2-dimethyl-cyclopropane-1-(R,S)-carboxylic acid were dissolved in 90 ml of carbon tetrachloride, and 8 g (0.05 mol) of bromine, dissolved in 10 ml of carbon tetrachloride, were slowly added dropwise at 20°-25° C., while stirring. Thereafter, the mixture was subsequently stirred at room temperature for 1 hour, the solvent was then stripped off in vacuo and the residue was stirred with 80 ml of n-hexane. The crystalline solid formed was filtered off. 15 g (68.6% of theory) of trans-3-(2-chloro-2-(4-chlorophenyl)-1,2-dibromoethyl)-2,2-dimethyl-cyclopropane-1-(R,S)-carboxylic acid were obtained as a light yellow solid with a melting point of 150° C.

The following compounds could be prepared analogously:

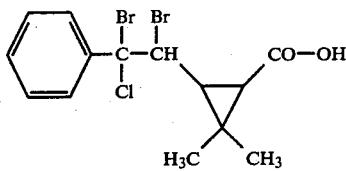 (b)

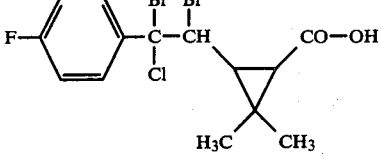

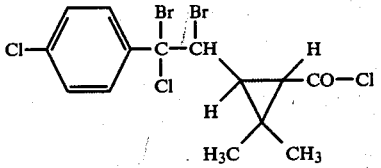

14 g of trans-3-(2-chloro-2-(4-chloro-phenyl)-1,2-dibromoethyl)-2,2-dimethyl-cyclopropane-1-(R,S)-carboxylic acid were dissolved in 100 ml of carbon tetrachloride, 75 g of thionyl chloride were added and the mixture was heated to the reflux temperature for 4 hours. The solvent and excess thionyl chloride were then stripped off in vacuo. 13.7 g (77.8% of theory) of trans-3-(2-chloro-2-(4-chloro-phenyl)-1,2-dibromoethyl)-2,2-dimethyl-cyclopropane-1-(R,S)-carboxylic acid chloride were obtained as a viscous oil.

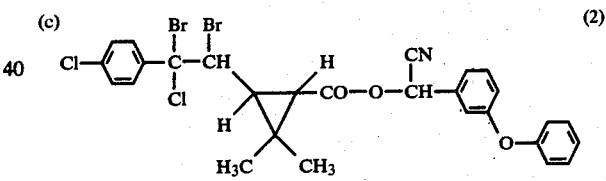 (2)

2.25 g (0.01 mol) of 3-phenoxy-α-cyanobenzyl alcohol and 4.63 g (0.01 mol) of trans-3-(2-chloro-2-(4-chloro-phenyl)-1,2-dibromoethyl)-2,2-dimethyl-cyclopropane-1-(R,S)-carboxylic acid chloride were dissolved in 100 ml of anhydrous toluene, and 0.8 g (0.01 mol) of pyridine, dissolved in 200 ml of toluene, was added dropwise at 25°-30° C., while stirring. The reaction mixture was then stirred for a further 3 hours at 25° C. It was poured into 150 ml of water and the organic phase was separated off and washed again with 100 ml of water. The toluene phase was then dried over sodium sulphate and the solvent was distilled off under a waterpump vacuum. Last residues of solvent were removed by brief incipient distillation at a bath temperature of 60° C./1 mm Hg. 6 g (92% of theory) of trans-3-(2-chloro-2-(4-chloro-phenyl)-1,2-dibromoethyl)-2,2-dimethylcyclopropane-1-(R,S)-carboxylic acid α-(R,S)-cyano-3-phenoxy-benzyl ester were obtained as a viscous oil. The structure was confirmed by the $^1$H-NMR spectrum.

$^1$H-NMR spectrum (in CDCl$_3$/TMS):

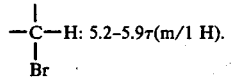

The compounds listed below could be prepared analogously to Example 1 or 2 (the $^1$H-NMR spectrum, where given, was measured in CDCl$_3$/TMS):

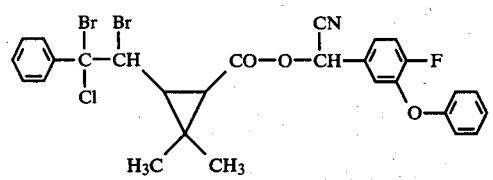

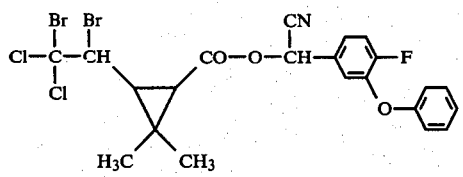

5.45–5.85τ(m/1 H) =
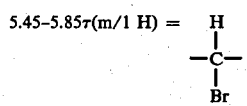

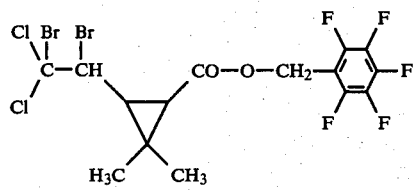

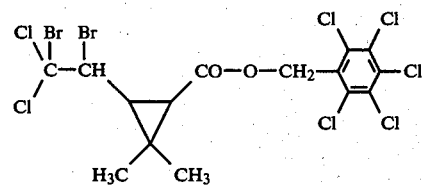

5.4–5.85τ(m/1 H) =
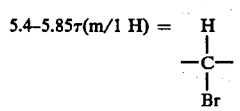

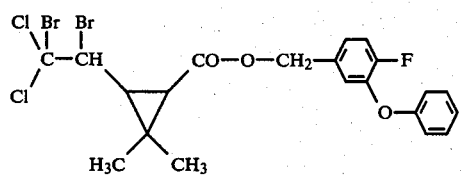

Refractive Index $n_D^{20}$: 1.5717.

The active compounds are well tolerated by plants, have a favorable level of toxicity to warm-blooded animals, and can be used for combating arthropod pests, especially insects and acarids, which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera* spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophea maderae, Blattella germanica, Acheta domesticus, Cryllotalpa* spp., *Locusta migratoria migratoriodides, Melanoplus differentialis* and *Schistocera gregaria;* from the order of the Dermaptera, for example *Forficular auricularia;* from the order of the Isoptera, for example *Reticulitermes* spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example *Eurygaster* spp., *Dysdercus intermedius, Piesma quadrata, Cimex lectularius, Rhodnius prolixus* and Triactoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chyrsorrhoea, Lymantria* spp., *Bucculatrix thurberiella, Phyllocnitis citrella, Agrotis* spp., *Euxoa* spp., Felitia spp., *Earias insulana, Heliothis* spp., *Laphygma exigua, Mamestra brassicae, Panolis flammea, Prodenia litura, Spodoptera* spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnamima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.0001 to 1% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The active compounds according to the invention are also suitable for combating ecto parasites and endo parasites in the field of veterinary medicine.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides a pesticidal composition containing as active ingredient a compound of the present invention in admixture with a solid or liquefied gaseous diluent or carrier or in admixture with a liquid diluent or carrier containing a surface-active agent.

The present invention also provides a method of combating pests (in particular arthropods and especially insects or acarids), which comprises applying to the pests, or to a habitat thereof, a compound of the present invention alone or in the form of a composition containing as active ingredient a compound of the present invention in admixture with a diluent or carrier.

The present invention also provides a method of freeing or protecting domesticated animals from parasites which comprises applying to said animals a compound according to the present invention, in admixture with a diluent or carrier.

The present invention further provides crops protected from damage by pests by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasites by the application to said animals of a compound according to the present invention, in admixture with a diluent or carrier.

The pesticidal activity of the compounds of this invention is illustrated by the following examples wherein the compounds according to the present invention are each identified by the number (given in brackets) from the preparative examples hereinabove:

Example 3

Phaedon larvae test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were treated by being dipped into the preparation of the active compound and were infested with mustard beetle larvae (*Phaedon cochleariae*), as long as the leaves were still wet.

After the specified periods of time, the degree of destruction was determined in %: 100% meant that all of the beetle larvae had been killed whereas 0% meant that none of the beetle larvae had been killed.

In this test, for example, the following compounds showed a superior activity compared with the prior art: (1) and (2).

Example 4

Test with *Stomoxys calcitrans*
Solvent:
  35 parts by weight of ethylene glycol monomethyl ether
  35 parts by weight of nonylphenol polyglycol ether To produce a suitable preparation of active compound, three parts by weight of active compound were mixed with seven parts by weight of the solvent mixture indicated above, and the concentrate thus obtained was diluted with water to the particular desired concentration.

10 adult *Stomoxys calcitrans* were placed in Petri dishes containing filter paper discs of appropriate size which had been saturated one day before the start of the experiment with 1 ml of the active compound preparation to be tested. After 3 hours, the degree of destruction was determined.

In this test, for example, the following compounds showed a superior action compared with the prior art: (1) and (2).

Example 5

Test with *Boophilus microplus* resistant
Solvent:
  35 parts by weight of ethylene glycol monomethyl ether
  35 parts by weight of nonylphenol polyglycol ether To produce a suitable preparation of active compound, three parts by weight of active compound were mixed with seven parts by weight of the solvent mixture indicated above, and the concentrate thus obtained was diluted with water to the desired concentration.

10 adult *Boophilus microplus* res. were immersed for 1 minute in the active compound preparation to be tested. After transfer to plastic beakers and storage in a climatically controlled chamber, the degree of destruction was determined.

In this test, for example, the following compounds showed a superior action compared with the prior art: (1) and (2).

Example 6

Test with *Musca autumnalis*
Solvent:
  35 parts by weight of ethylene glycol monomethyl ether
  35 parts by weight of nonylphenol polyglycol ether To produce a suitable preparation of active compound, three parts by weight of active compound were mixed with seven parts by weight of the abovementioned solvent mixture and the concentrate thus obtained was diluted with water to the particular desired concentration.

10 *Musca autumnalis* adults were introduced into Petri dishes containing filter paper discs of appropriate size which had been saturated one day before the start of the experiment with 1 ml of the preparation of active compound to be tested. After 3 hours, the degree of destruction was determined.

In this test, for example, the following compounds showed a superior action compared with the prior art: (1) and (2).

Example 7

Test with *Lucilia cuprina* res. larvae
Solvents:
  35 parts by weight of ethylene glycol monomethyl ether
  35 parts by weight of nonylphenol polyglycol ether To produce a suitable preparation of active compound, three parts by weight of active compound were mixed with seven parts by weight of the abovementioned solvent mixture and the concentrate thus obtained was diluted with water to the particular desired concentration.

About 20 *Lucilia cuprina* res. larvae were introduced into a test tube which contained approx. 1 cm$^3$ of horse muscle and 0.5 ml of the preparation of active compound. After 24 hours, the degree of destruction was determined.

In this test, for example, the following compounds showed a superior action compared with the prior art: (1) and (2).

Example 8

Critical concentration test/soil insects
Test insect: *Agrotis segetum* larvae (in the soil)
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (=mg/l). The treated soil was filled into pots and the pots were left to stand at room temperature.

After 24 hours the test insects were introduced into the treated soil and after a further 2 to 7 days the degree of effectiveness of the active compound was determined in % by counting the dead and the live test insects. The degree of effectiveness was 100% if all of the test insects had been killed and was 0% is exactly as many test insects were still alive as in the case of the untreated control.

In this test, for example, the following compound showed a superior action compared with the prior art: (2).

It will be understood that the specification and examples are illustrative but not limitative of the present invention and that other embodiments within the spirit and scope of the invention will suggest themselves to those skilled in the art.

We claim:

1. A substituted 3-(1,2-dibromo-alkyl)-2,2-dimethyl-cyclopropane-1-carboxylic acid ester of the formula

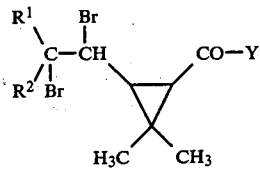

in which
$R^1$ is phenyl optionally substituted by at least one of halogen, optionally halogen-substituted $C_1$-$C_4$ alkyl, $C_1$-$C_4$-alkoxy, $C_1$-$C_4$-alkylthio or $C_1$-$C_2$-alkylenedioxy,
$R^2$ is hydrogen, halogen or optionally halogen-substituted $C_1$-$C_4$-alkyl,
Y is

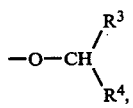

$R^3$ is hydrogen, cyano or optionally substituted alkyl, alkenyl or alkynyl, and
$R^4$ is phenyl which is substituted by at least one of halogen and phenoxy which is itself optionally substituted by halogen, alkyl or halogenoalkyl, with the proviso that the phenyl radical contains at least one halogen substituent if $R^1$ represents methyl or halogen.

2. A compound according to claim 1, wherein such compound is trans-3-(2-chloro-2-(4-chlorophenyl)-1,2-dibromoethyl)-2,2-dimethyl-cyclopropane-1-(R,S)-carboxylic acid α-(R,S)-cyano-3-phenoxy-4-fluoro-benzyl ester of the formula

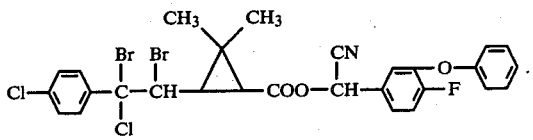

3. A compound according to claim 1, wherein such compound is trans-3-(2-chloro-2-(4-chloro-phenyl)-1,2-dibromoethyl)-2,2-dimethyl-cyclopropane-1-(R,S)-carboxylic acid α-(R,S)-cyano-3-phenoxy-benzyl ester of the formula

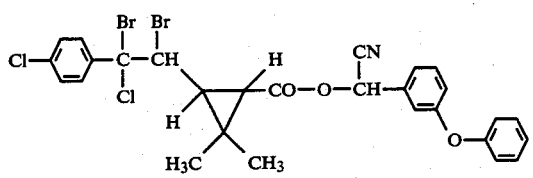

4. A compound according to claim 1, wherein such compound is trans-3-(2-chloro-2-phenyl-1,2-dibromoethyl)-2,2-dimethyl-cyclopropane-1-(R,S)-carboxylic acid α-(R,S)-cyano-3-phenoxy-4-fluoro-benzyl ester of the formula

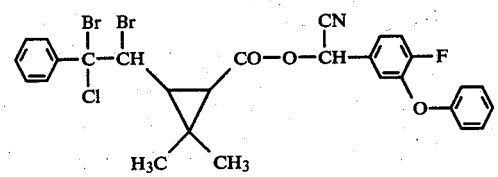

5. A pesticidal composition comprising a pesticidally effective amount of a compound according to claim 1 in admixture with a diluent.

6. A compound according to claim 1, wherein $R^4$ is fluorine-substituted phenoxyphenyl.

7. A method of combating pests comprising applying to the pests, or to a habitat thereof, a pesticidally effective amount of a compound according to claim 1.

8. The method according to claim 7, wherein such pests are insects or acarids and the compound is
trans-3-(2-chloro-2-(4-chlorophenyl)-1,2-dibromoethyl)-2,2-dimethyl-cyclopropane-1-(R,S)-carboxylic acid α-(R,S)-cyano-3-cyano-3-phenoxy-4-fluorobenzyl ester,
trans-3-(2-chloro-2-(4-chloro-phenyl)-1,2-dibromoethyl(-2,2-dimethyl-cyclopropane-1-(R,S)-carboxylic acid α-(R,S)-cyano-3-phenoxy-benzyl ester or,
trans-3-(2-chloro-2-phenyl-1,2-dibromoethyl)-2,2-dimethyl-cyclopropane-1-(R,S)-carboxylic acid α-(R,S)-cyano-3-phenoxy-4-fluoro-benzyl ester.

9. A 3-(1,2-dibromo-alkyl)-2,2-dimethylcyclopropane-1-carboxylic acid derivative of the formula

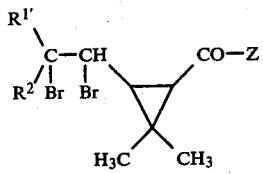

in which

R$^{1'}$ is phenyl optionally substituted by at least one of halogen, optionally halogen-substituted C$_1$–C$_4$ alkyl, C$_1$–C$_4$ alkoxy, C$_1$–C$_4$-alkylthio or C$_1$–C$_2$-alkylenedioxy, R$^2$ is hydrogen, halogen or optionally halogen-substituted C$_1$–C$_4$-alkyl, Z is hydroxyl, chlorine, C$_1$–C$_4$-alkoxy or O$^\ominus$M$^\oplus$, and M$^\oplus$ is an ammonium ion or one alklai metal or alkaline earth metal ion equivalent.

* * * * *